US012740735B2

(12) United States Patent
Natarajan

(10) Patent No.: US 12,740,735 B2
(45) Date of Patent: Sep. 22, 2026

(54) SCORE INDICATIVE OF MINDFULNESS OF A USER

(71) Applicant: Google LLC, Mountain View, CA (US)

(72) Inventor: Aravind Natarajan, San Francisco, CA (US)

(73) Assignee: GOOGLE LLC, Mountain View, CA (US)

( * ) Notice: Subject to any disclaimer, the term of this patent is extended or adjusted under 35 U.S.C. 154(b) by 312 days.

(21) Appl. No.: 18/044,470

(22) PCT Filed: Oct. 20, 2022

(86) PCT No.: PCT/US2022/047255

§ 371 (c)(1),
(2) Date: Mar. 8, 2023

(87) PCT Pub. No.: WO2024/030141

PCT Pub. Date: Feb. 8, 2024

(65) Prior Publication Data

US 2025/0072798 A1 Mar. 6, 2025

Related U.S. Application Data

(60) Provisional application No. 63/395,594, filed on Aug. 5, 2022.

(51) Int. Cl.

| | |
|---|---|
| ***A61B 5/00*** | (2006.01) |
| ***A61B 5/024*** | (2006.01) |
| ***A61B 5/16*** | (2006.01) |

(52) U.S. Cl.

CPC .......... *A61B 5/165* (2013.01); *A61B 5/02405* (2013.01); *A61B 5/681* (2013.01);

(Continued)

(58) Field of Classification Search

None

See application file for complete search history.

(56) References Cited

U.S. PATENT DOCUMENTS

| | | | |
|---|---|---|---|
| 4,354,505 | A | 10/1982 | Shiga |
| 2014/0335486 | A1 | 11/2014 | Honigsberg |

(Continued)

FOREIGN PATENT DOCUMENTS

| | | |
|---|---|---|
| JP | H 07275219 | 10/1995 |
| JP | 2013/128659 | 7/2013 |
| JP | 2021/536307 | 12/2021 |

OTHER PUBLICATIONS

International Search Report for PCT/US2022/047255, mailed on Feb. 7, 2023, 2 pages.

(Continued)

*Primary Examiner* — Sana Sahand

(74) *Attorney, Agent, or Firm* — DORITY & MANNING P.A.

(57) ABSTRACT

A computer-implemented method for determining a score indicative of mindfulness of a user is provided. The method includes obtaining heart rate variability data of the user during a guided breathing exercise in which the user inhales and exhales to mimic a respiration rate associated with mindfulness. The method includes filtering the heart rate variability data to generate filtered heart rate variability. The method includes determining a first standard deviation of interbeat intervals indicative of respiratory sinus arrythmia and included in a first segment of the filtered heart rate variability data that spans a discrete interval of time. The method includes determining a second standard deviation of all interbeat intervals included in the first segment of the filtered heart rate variability data. The method includes determining a score indicative of mindfulness of the user (Continued)

based on the first standard deviation and the second standard deviation.

16 Claims, 9 Drawing Sheets

(52) U.S. Cl.
CPC .......... *A61B 5/7225* (2013.01); *A61B 5/7257* (2013.01); *A61B 5/742* (2013.01)

(56) References Cited

U.S. PATENT DOCUMENTS

| | | | | |
|---|---|---|---|---|
| 2015/0351655 | A1 | 12/2015 | Coleman | |
| 2017/0188976 | A1 | 7/2017 | Kalra et al. | |
| 2019/0223773 | A1 * | 7/2019 | Galm | A61B 5/165 |
| 2019/0247010 | A1 | 8/2019 | Barnacka | |
| 2022/0175309 | A1 | 6/2022 | Vardas et al. | |
| 2023/0240545 | A1 | 8/2023 | Moore et al. | |

OTHER PUBLICATIONS

Extended European Search Report for Application No. EP 22859455.2, mailed Jul. 11, 2024, 7 pages.
Bortolla et a1., “Mindfulness Effects on Mind Wandering and Autonomic Balance”, Applied Psychophysiology and Biofeedback, Nov. 6, 2021, 12 pages.
International Preliminary Report on Patentability for Application No. PCT/US2022/047255, mailed Feb. 20, 2025, 7 pages.

* cited by examiner

SCORE INDICATIVE OF MINDFULNESS OF A USER

PRIORITY CLAIM

The present application claims priority to U.S. Patent Application No. 63/395,594, titled "Score Indicative of Mindfulness of a User," having a filing date of Aug. 5, 2022, which is incorporated by reference herein.

FIELD

The present disclosure relates generally to wearable computing devices. More particularly, the present disclosure relates to a method for determining a score indicative of mindfulness of a user during a meditation session based on biometric data obtained from a wearable computing device worn by the user.

BACKGROUND

Guided breathing exercises can be helpful in the management of stress. Wearable computing devices that can be worn, for instance, on a user's wrist can include a software application (e.g., app) that can facilitate a guided breathing exercise. For instance, the software application can cause the wearable computing device to display notifications that prompt the user to inhale and exhale at a rate that is conducive to mindfulness (e.g., meditation).

SUMMARY

Aspects and advantages of embodiments of the present disclosure will be set forth in part in the following description, or can be learned from the description, or can be learned through practice of the embodiments.

In one aspect, a computer-implemented method for determining a score indicative of mindfulness of a user performing a guided breathing exercise is provided. The method includes obtaining heart rate variability data of the user performing the guided breathing exercise. The method includes filtering the heart rate variability data to generate filtered heat rate variability data. The method includes determining a first standard deviation of interbeat intervals indicative of respiratory sinus arrythmia and included in a first segment of the filtered heart rate variability data that spans a discrete interval of time. The method includes determining a second standard deviation of all interbeat intervals included in the first segment of the filtered heart rate variability data. The method includes determining a score indicative of mindfulness of the user for the discrete interval of time based, at least in part, on the first standard deviation and the second standard deviation.

In some implementations, the method includes causing a display screen of a wearable computing device worn by the user to display the score indicative of mindfulness of the user for the discrete interval of time.

In some implementations, determining the score indicative of mindfulness of the user for the discrete interval of time includes determining the score based on a ratio of the first standard deviation of the interbeat interval indicative of respiratory sinus arrythmia and included in the first segment of the filtered heart rate variability data to the second standard deviation of all interbeat intervals included in the first segment of the filtered heart rate variability data.

In some implementations, determining the first standard deviation of interbeat intervals indicative of respiratory sinus arrythmia includes applying a Fourier transform to the first segment of the filtered heart rate variability data to obtain a normalized power spectral density function. Furthermore, determining the first standard deviation includes determining a peak amplitude of the normalized power spectral density function, fitting a Gaussian function to the peak amplitude, and determining the first standard deviation based, at least in part, on the Gaussian function.

In some implementations, determining the first standard deviation based, at least in part, on the Gaussian function includes integrating the Gaussian function over the discrete interval of time to determine an area under the Gaussian function.

In some implementations, the method includes causing a display screen of a wearable computing device worn by the user to display the score indicative of mindfulness of the user for the discrete interval of time and the respiration rate of the user for the discrete interval of time.

In some implementations, filtering the heart rate data includes applying a low-pass filter to the heart rate variability data.

In some implementations, the discrete interval of time is about 2 minutes.

In some implementations, the score indicative of mindfulness of the user for the discrete interval of time ranges from 0 to 100. Furthermore, in such implementations, the score indicates the user is being mindful for the discrete interval of time when the score is greater than a first numerical value. Additionally, the score indicates the user is stressed for the discrete interval of time when the score is less than a second numerical value that is less than the first numerical value.

In another aspect, a wearable computing device is provided. The wearable computing device includes one or more biometric sensors. The wearable computing device further includes one or more processors. The one or more processors are configured to obtain, via the one or more biometric sensors, heart rate variability data of a user wearing the wearable computing device and performing a guided breathing exercise. The one or more processors are configured to filter the heart rate variability data. The one or more processors are configured to determine a first standard deviation of interbeat intervals indicative of respiratory sinus arrythmia and included in a first segment of the filtered heart rate variability data. The one or more processors are configured to determine a second standard deviation of all interbeat interval s included in the first segment of the filtered heart rate variability data. The method includes determining a score indicative of mindfulness of the user for the discrete interval of time based, at least in part, on the first standard deviation and the second standard deviation.

In some implementations, the one or more processors are configured to determine mindfulness of the user for the discrete interval of time based, at least in part, on a ratio of the first standard deviation to the second standard deviation.

In some implementations, the one or more processors are further configured to cause a display screen to display the score indicative of mindfulness of the user for the discrete interval of time.

In some implementations, to determine the first standard deviation the one or more processors are configured to apply a Fourier transform to the first segment of the filtered heart rate variability data to obtain a normalized power spectral density function. The one or more processors are further configured to determine a peak amplitude of the normalized power spectral density function, fit a Gaussian function to the peak amplitude, and determine the first standard deviation based, at least in part, on the Gaussian function.

In some implementations, to determine the first standard deviation the one or more processors are configured to integrate the Gaussian function over the discrete interval of time to determine an area under the Gaussian function.

In some implementations, the one or more processors are configured to cause a display screen to display the score indicative of mindfulness of the user for the discrete interval of time as well as display the respiration rate of the user for the discrete interval of time.

In some implementations, the one or more processors are configured to apply a low-pass filter to the heart rate variability data to obtain the filtered heart rate variability data.

In some implementations, the score indicative of mindfulness of the user for the discrete interval of time ranges from 0 to 100. Furthermore, in such implementations, the score indicates the user is being mindful for the discrete interval of time when the score is greater than a first numerical value. Additionally, the score indicates the user is stressed for the discrete interval of time when the score is less than a second numerical value that is less than the first numerical value.

In yet another aspect, a computer-implemented method for determining mindfulness of a user performing a guided breathing exercise is provided. The method includes obtaining heart rate variability data of the user performing the guided breathing exercise. The method includes determining a first standard deviation of interbeat intervals indicative of respiratory sinus arrythmia and included in a first segment of the heart rate variability data that spans a discrete interval of time. The method includes determining a second standard deviation of all interbeat intervals included in the first segment of the heart rate variability data. The method includes determining a score indicative of mindfulness of the user for the discrete interval of time based, at least in part, on the first standard deviation and the second standard deviation.

In some implementations, determining the score indicative of mindfulness of the user for the discrete interval of time includes determining the score based on a ratio of the first standard deviation of the interbeat interval indicative of respiratory sinus arrythmia and included in the first segment of the heart rate variability data to the second standard deviation of all interbeat intervals included in the first segment of the filtered heart rate variability data.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Figure 1:
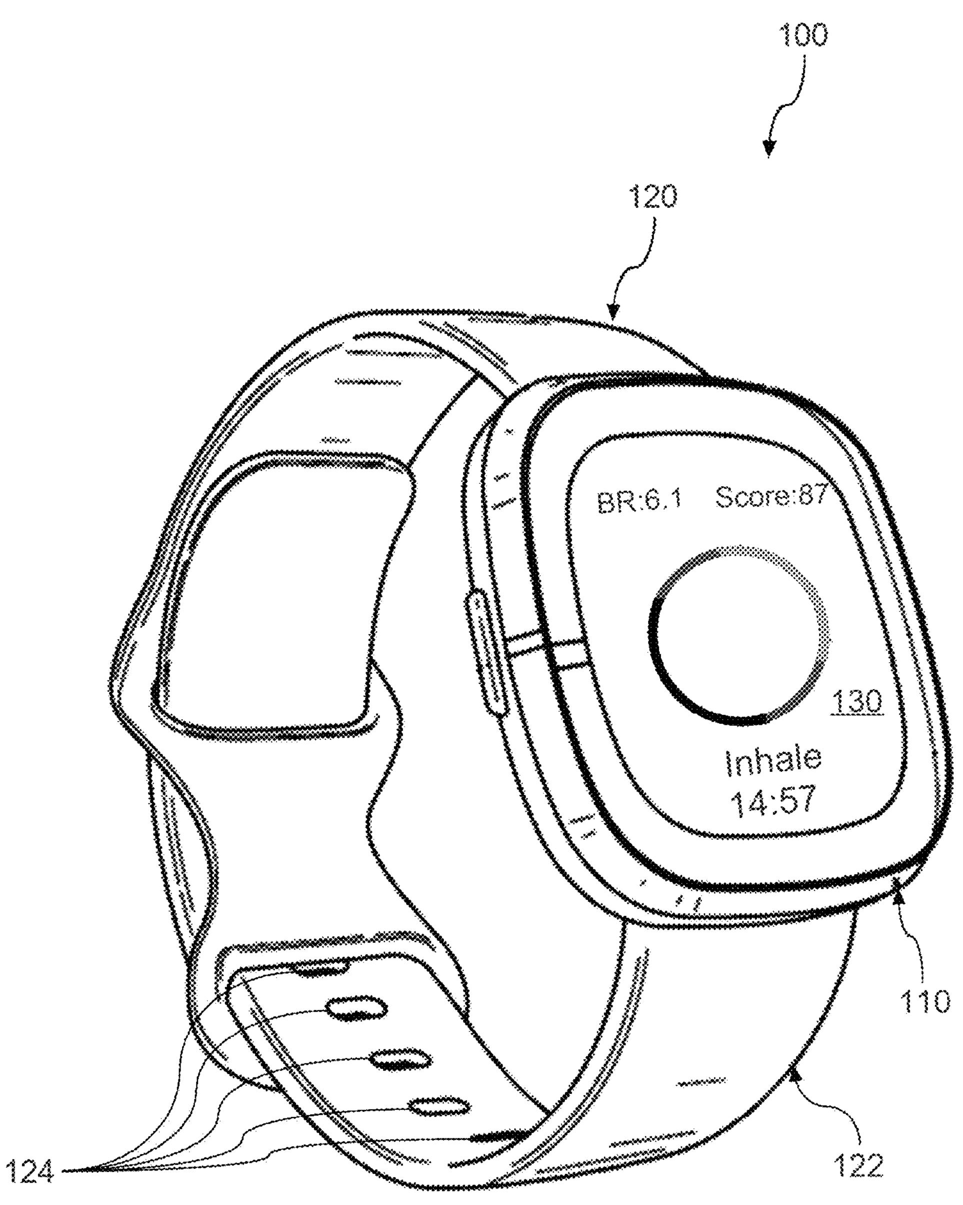
FIG. 1 depicts a wearable electronic device according to an embodiment of the present disclosure.

Reference now will be made in detail to embodiments of the present disclosure, one or more examples of which are illustrated in the drawings. Each example is provided by way of explanation of the present disclosure, not limitation of the present disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present invention covers such modifications and variations as come within the scope of the appended claims and their equivalents.

Example aspects of the present disclosure are directed to wearable computing devices. A wearable computing device can, for instance, be worn on a user's wrist. The wearable computing device can include one or more biometric sensors (e.g., optical sensors). For instance, the one or more biometric sensors can be configured to obtain heart rate variability (HRV) data of a user wearing the wearable computing device. Furthermore, the wearable computing device can be configured to instruct the user to perform a guided breathing exercise. For instance, the wearable computing device can display notifications prompting the user to inhale for a predetermined amount of time and then exhale for a predetermined amount of time to attain a breathing rate (e.g., about 3 breaths per minute) needed for the user to achieve "mindfulness" during the guided breathing exercise. As used herein, the term "mindfulness" refers to a state in which a parasympathetic branch of the user's autonomic nervous system (ANS) is more dominant than a sympathetic branch of the user's ANS. It should be understood that breathing at the desired breathing rate needed to achieve mindfulness results in a rhythmic oscillation of the user's heart rate at the respiration frequency.

Example aspects of the present disclosure are directed to determining an autonomic balance index (ABI) or score indicative of mindfulness of the user during the guided breathing exercise. The score can be determined from the HRV data obtained via the one or more biometric sensors of the wearable computing device worn by the user during the guided breathing exercise. In some embodiments, the HRV data from which the score is determined can be preprocessed to remove noise therefrom. For instance, in some embodiments, the HRV data can be low-pass filtered (e.g., using a median filter). It should be understood that data points in the HRV data that are a predetermined number of standard deviations (e.g., about 3) from a length of the low-pass filter can be labeled as an outlier and removed from the filtered HRV data. Furthermore, it should be understood that the HRV data can be iteratively low-pass filtered until all data points that make up the filtered HRV data are less than the predetermined number of standard deviations from the length of the low-pass filter.

The filtered HRV data can be divided into a plurality of segments. Furthermore, each of the segments can span a discrete interval of time during which the user's respiration rate can be considered substantially constant. For instance, in some embodiments, the discrete interval of time can be about 2 minutes.

In some embodiments, the score indicative of mindfulness of the user can be determined for each of the plurality of segments of the filtered HRV data. In this manner, the score indicative of mindfulness of the user can be determined for each successive discrete interval of time (e.g., about 2 minutes). As used herein, the term "about" when used in conjunction with a stated numerical value refers to a range of values within 10 percent of the stated numerical value.

In some embodiments, a first segment of the filtered HRV data can be passed through a smoothing filter (e.g., a Hann filter). Alternatively, or additionally, a Fourier transform can be performed on the first segment of the filtered HRV data to generate a power spectral density (PSD) of the first segment of the filtered HRV data. From the PSD of the first segment of the filtered HRV data, a peak amplitude of the PSD can be determined. The peak amplitude of the PSD can correspond to a respiration frequency associated with respiratory sinus arrhythmia, which is a reliable measure of the parasympathetic branch of the autonomic nervous system.

In some embodiments, a Gaussian function can be fitted to the peak amplitude of the PSD. Furthermore, an area under the Gaussian function can be indicative of a standard deviation of interbeat intervals included within the first segment of filtered HRV data that are indicative of respiratory sinus arrhythmia. Accordingly, the Gaussian function can be integrated over the discrete interval of time to determine the standard deviation of the interbeat intervals included in the first segment of the filtered HRV data that are indicative of respiratory sinus arrhythmia.

A score indicative of the mindfulness of the user during the interval of time (e.g., 2 minutes) associated with the first segment of filtered HRV data can be determined based, at least in part, on, e.g., a ratio of the standard deviation of interbeat intervals included in the first segment of the filtered HRV data that are indicative of respiratory sinus arrhythmia to a standard deviation of all interbeat intervals included in the first segment of the filtered HRV data. For instance, the score can include a numerical value that ranges from 0 to 100. When the score is above a first numerical value (e.g., about 75), the score can indicate the user achieved mindfulness for the discrete interval of time. Conversely, the score can indicate the user was stressed for the discrete interval of time and therefore did not achieve mindfulness when the score is less than a second numerical value (e.g., about 50) that is less than the first numerical value. In some embodiments, the score can indicate the user is asleep or in a meditative zone with distractions when the score is greater than or equal to the second numerical value (e.g., about 50) but less than the first numerical value (e.g., about 75).

In some embodiments, a score indicative of mindfulness of the user can be determined for each successive discrete interval of time (e.g., about every 2 minutes) by processing each successive segment of the filtered HRV data. In this manner, how many minutes of the guided breathing exercise were "mindful minutes" during which the user achieved mindfulness can be determined.

In some embodiments, the score indicative of mindfulness can be displayed on a display screen of the wearable computing device in real-time or near real-time while the user is performing the guided breathing exercise. In this manner, the user can receive real-time or near real-time feedback on whether the user is achieving mindfulness during the guided breathing exercise. Furthermore, in some embodiments, a breathing rate of the user can be displayed on the display screen of the wearable computing device. In this manner, the user can know whether his or her breathing rate is too fast and therefore preventing the user from achieving mindfulness during the guided breathing exercise.

In some embodiments, the score indicative of mindfulness of the user for each successive discrete interval of time (e.g., about every 2 minutes) can be stored in one or more memory device. In this manner, the user can access the scores stored in the one or more memory devices to monitor the user's mindfulness throughout the guided breathing exercise. For instance, the user can gain insight into how mindful the user was at various points (e.g., beginning, middle, and end) of the guided breathing exercise.

In some embodiments, the scores indicative of mindfulness for each of the different segments of the filtered heart rate variability data can be stored locally on wearable electronic device. In this manner, the user can access the scores without needing a network connection (e.g., Internet connection). In alternative embodiments, the one or more memory devices can be on a device (e.g., server, mobile computing device, etc.) that is remote relative to the wearable electronic device. In this manner, memory on the wearable electronic device can be conserved.

Example aspects of the present disclosure provide numerous technical effects and benefits. For instance, filtering the heart rate variability data can remove noise associated with the heart rate variability obtained from the sensors (e.g., electrodes) on the wearable electronic device and can therefore improve the accuracy of the score indicative of mindfulness of the user. Thus, the score can be a more reliable metric of how mindful the user is being during the guided breathing exercise. Furthermore, displaying the respiration rate of the user in conjunction with the score can provide additional insight on the user's score for a particular segment of the filtered heart rate data. For instance, the respiration rate can be high when the score indicative of mindfulness is low. Thus, the user can see that their score for a particular segment is low due, at least in part, to the user breathing faster than the respiration rate in which the user can achieve mindfulness.

Figure 2:
FIG. 2 depicts a rear perspective view of a wearable electronic device according to an embodiment of the present disclosure.
Figure 2:
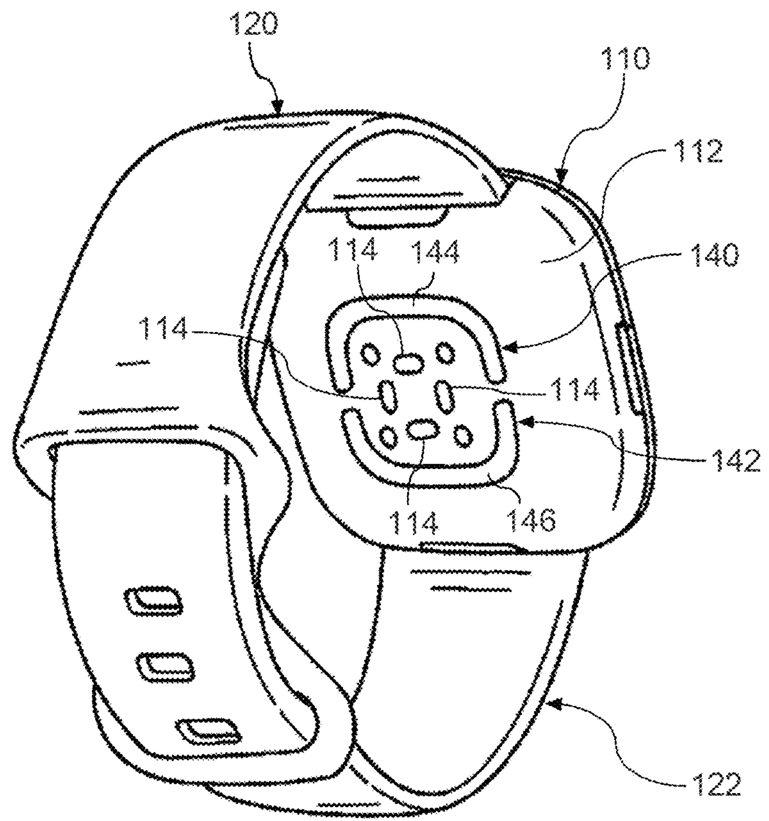

Referring now to the FIGS., FIGS. 1 and 2 depict a wearable electronic device 100 according to some embodiments of the present disclosure. The wearable electronic device 100 can be worn, for instance, on an arm (e.g., wrist) of a user. The wearable electronic device 100 can include a housing 110 and one or more electronic components (e.g., disposed on printed circuit boards) disposed within an internal cavity defined by the housing 110. Furthermore, the wearable electronic device 100 can include a battery (not shown) that is disposed within the internal cavity of the housing 110.

In some embodiments, the wearable electronic device 100 can include a first band 120 coupled to the housing 110 at a first location and a second band 122 coupled to the housing 110 at a second location. The first band 120 and the second band 122 can be coupled to one another to secure the housing 110 to the arm of the user. For instance, the first band 120 can include a buckle or clasp (not shown). Additionally, the second band 122 can define a plurality of apertures 124 spaced apart from one another along a length of the second band 122. In such embodiments, a prong of the buckle associated with the first band 120 can extend through one of the plurality of openings defined by the second band 132 to couple the first band 120 to the second band 122.

It should be appreciated that the first band 120 can be coupled to the second band 122 using any suitable type of fastener. For instance, in some embodiments, the first band 120 and the second band 122 can include a magnet. In such embodiments, the first band 120 and the second band 122 can be magnetically coupled to one another to secure the housing 110 to the arm of the user.

In some embodiments, the wearable electronic device 100 can include a display 130 configured to display content (e.g., time, date, biometric, notifications, etc.) for viewing by the user. For instance, the display 130 can include a plurality of pixels. In some embodiments, the display 130 can include an organic light emitting diode (OLED) display. It should be understood, however, that the display 130 can include any suitable type of display.

The wearable electronic device 100 can include a first electrode 140 and a second electrode 142. It should be understood that the wearable electronic device 100 can include more or fewer electrodes. As shown, the first electrode 140 and the second electrode 142 can, in some embodiments, be positioned on a lower portion (e.g., wrist-facing side) of the housing 110. More specifically, the electrodes 140, 142 can be positioned within respective apertures (e.g., cutouts) defined by the lower portion of the housing 110. In this manner, the first electrode 140 and the second electrode 142 can each contact (e.g., touch) the user's skin (e.g., wrist) when the user is wearing the wearable electronic device 100. Furthermore, since the electrodes 140, 142 contact the user's skin, the electrodes 140, 142 can be used to measure one or more biometrics (e.g., electrodermal activity, electrocardiogram) of the user.

In some implementations, the wearable electronic device 100 can, in some embodiments, include one or more optical sensors (e.g., photoplethysmography (PPG) sensors) disposed within an interior cavity defined by the housing 110. The optical sensor(s) can be configured to emit a light signal (e.g., infrared light) that passes through a transparent portion 114 of the housing 110. For instance, in some embodiments, the transparent portion 114 of the housing 110 can include one or more windows that are transparent and positioned at different locations (e.g., cutouts) on the housing 110. It should be understood that the light signal exits the interior cavity of the housing 110 via the transparent portion 114 thereof, penetrates the user's skin and blood vessels, and returns to the optical sensor(s) as a reflected light signal. It should be understood, using the disclosures provided herein, that one or more biometrics associated with the user can be determined based, at least in part, on the reflected light signal.

Figure 3A:
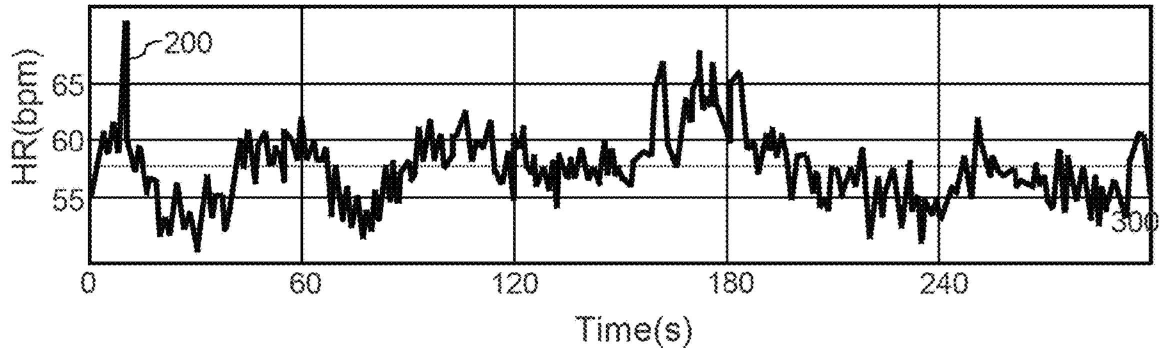
FIG. 3A depicts a graphical representation of the heart rate of a user while the user is stressed according to an embodiment of the present disclosure.
Figure 3B:
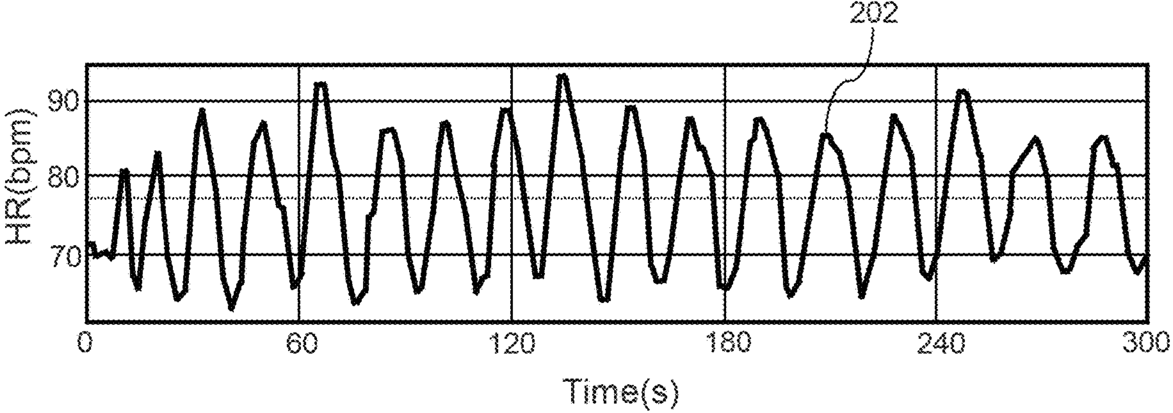
FIG. 3B depicts a graphical representation of the heart rate of a user while the user is engaging in meditation according to an embodiment of the present disclosure.

Referring now to FIGS. 3A and 3B, graphical representations of a user's heart rate are provided according to embodiments of the present disclosure. More particularly, FIG. 3A illustrates a time-varying signal 200 that is indicative of a user's heart rate over a period of time (e.g., 300 seconds) during which the user is stressed. Conversely, FIG. 3B illustrates a time-varying signal 202 that is indicative of the user's heart rate as a function of time when the user is meditating (e.g., performing a guided breathing exercise). As shown, the user's heart rate during meditation exhibits a consistent rhythmic oscillation that is needed to achieve mindfulness and therefore reduce stress. As will now be discussed, example aspects of the present disclosure are directed to determining a score indicative of mindfulness of the user during a meditation session (e.g., guided breathing exercise) to provide insight into the effectiveness of the meditation session on reducing the user's stress.

Figure 4:
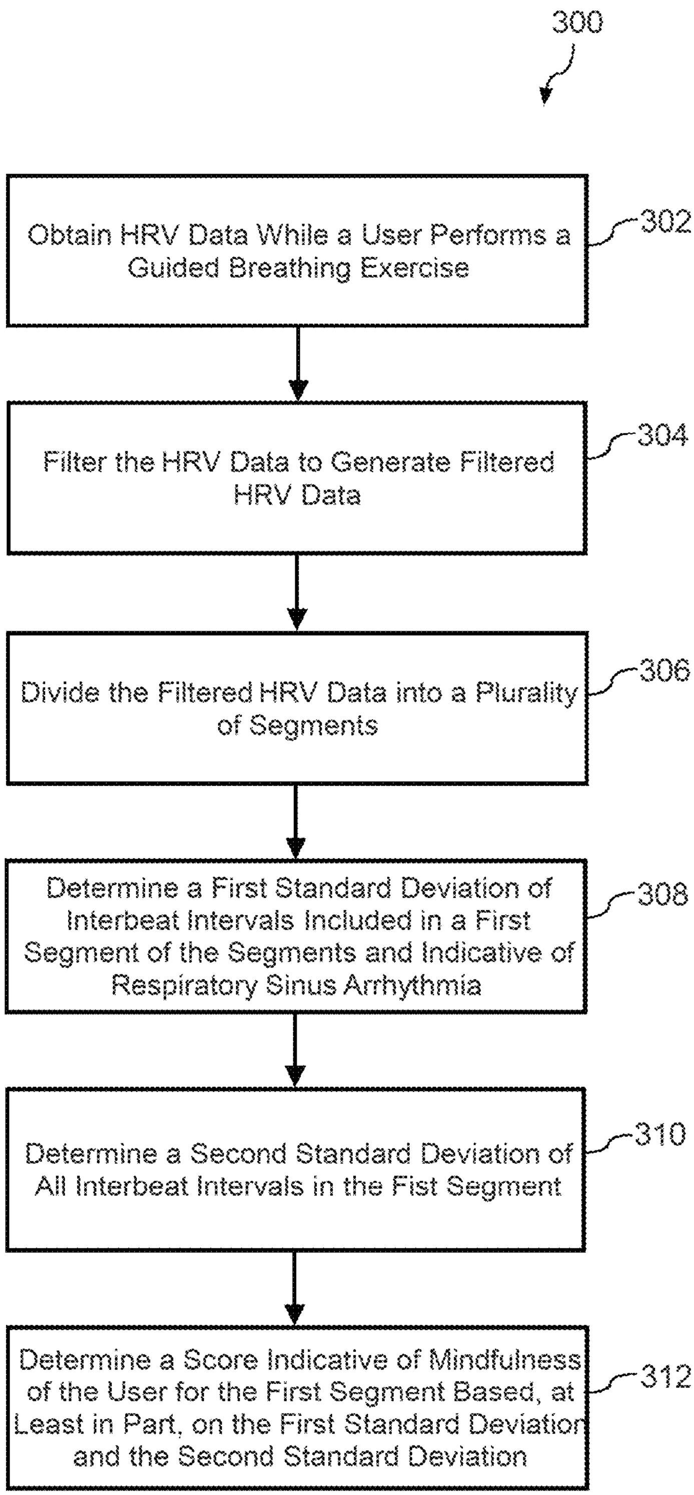
FIG. 4 depicts a flow diagram of a method for determining a score indicative of mindfulness of a user according to an embodiment of the present disclosure.

Referring now to FIG. 4, a flow diagram of an example method 300 for determining a score indicative of mindfulness of a user during a guided breathing exercise. The method 300 can be implemented by, for instance, one or more processors. In some embodiments, the one or more processors can be part of the wearable computing device discussed above with reference to FIGS. 1 and 2. In alternative embodiments, the one or more processors can be distributed between the wearable computing device and a computing device that is separate from the wearable computing device and communicatively coupled to the wearable computing device over a wireless network. FIG. 3 depicts steps performed in a particular order for purposes of illustration and discussion. Those of ordinary skill in the art, using the disclosures provided herein, will understand that various steps of method 300 or any of the other methods disclosed herein may be adapted, modified, rearranged, performed simultaneously, or modified in various ways without deviating from the scope of the present disclosure.

At (302), the method 300 can include obtaining heart rate variability data for the user while the user performs a guided breathing exercise in which the user inhales for a predetermined amount of time and exhales for a predetermined amount of time to mimic a respiration rate associated with mindfulness. For example, the heart rate variability data can be determined based, at least in part, on data obtained via one or more biometric sensors (e.g., optical sensors) of the wearable computing device.

At (304), the method 300 can include filtering the heart rate variability data to generate filtered heart rate variability data. For example, in some embodiments, one or more processors can low-pass filter the heart rate variability data obtained at (202) to generate filtered heart rate variability data. In some embodiments, the heart rate variability can be passed through a median filter of length n. In such embodiments, data points in the filtered heart rate variability data that are greater than n standard deviations from the mean of the median filter can be flagged as outliers and removed from the filtered heart rate variability data. In some embodiments, multiple iterations of filtering the heart rate variability data can be performed until all data points in the filtered heart rate variability are less than n standard deviations from the mean of the median filter.

At (306), the method 300 can include dividing the heart rate variability data into a plurality of segments. Each of the plurality of segments can span a discrete interval of time. For instance, the discrete interval of time can correspond to an amount of time during which the user's respiration rate is substantially constant. In some embodiments, the discrete interval of time can be about 2 minutes.

At (308), the method 300 can include determining a first standard deviation of interbeat intervals included in a first segment of the plurality of segments and indicative of respiratory sinus arrhythmia. For example, a Fourier transform can be performed on the first segment of the filtered HRV data to generate a power spectral density (PSD) of the first segment of filtered HRV data. From the PSD of the first segment of filtered HRV data, a peak amplitude of the PSD can be determined. The peak amplitude of the PSD can correspond to a respiration frequency associated with respiratory sinus arrhythmia, which is a reliable measure of the parasympathetic branch of the autonomic nervous system.

In some embodiments, a Gaussian function can be fitted to the peak amplitude of the PSD. Furthermore, an area under the Gaussian function can be indicative of a standard deviation of interbeat intervals included within the first segment of filtered HRV data that are indicative of respiratory sinus arrhythmia. Accordingly, the Gaussian function can be integrated over to determine the standard deviation of the interbeat intervals included within the first segment of filtered HRV data that are indicative of respiratory sinus arrhythmia.

At (310), the method 300 can include determining a second standard deviation of all interbeat intervals included in the first segment of HRV data.

At (312), the method 300 can include determining a score indicative of the mindfulness of the user for an interval of time (e.g., 2 minutes) associated with the first segment of filtered HRV data. The score can be determined based, at least in part, on the standard deviation of interbeat intervals included in the first segment of filtered HRV data that are indicative of respiratory sinus arrhythmia and a standard deviation of all interbeat intervals included in the first segment of filtered HRV data, e.g., based on a ratio of the standard deviation of interbeat intervals included in the first segment of filtered HRV data that are indicative of respiratory sinus arrhythmia to the standard deviation of all interbeat intervals included in the first segment of filtered HRV data. For instance, the score can include a numerical value that ranges from 0 to 100. When the score is above a first numerical value (e.g., about 75), the score can indicate the user achieved mindfulness during the interval of time. Conversely, the second can indicate the user was stressed and therefore did not achieve mindfulness when the score is less than a second numerical value (e.g., about 50) that is smaller than the first numerical value. In some embodiments, the score can indicate the user is asleep or in a meditative zone with distractions when the score is greater than or equal to the second numerical value (e.g., about 50) but less than the first numerical value (e.g., about 75).

At (314), the method 300 can include causing a display screen of a wearable computing device worn by the user performing the guided breathing exercise to display the score determined at (212). For instance, the display 130 of the wearable computing device 100 discussed above with reference to FIG. 1 is shown displaying a score of 87 to indicate that the user is achieving mindfulness while performing the guided breathing exercise. Furthermore, the display 130 of the wearable computing device 100 is shown displaying a breathing rate (that is. 6.1 breaths per minute) of the user. By doing so, the user can better understand the relationship between breathing rate and mindfulness.

In some embodiments, the score indicative of mindfulness of the user can be determined for each successive interval of time (e.g., about every 2 minutes) by processing each successive segment of the filtered HRV data. In such embodiments, the score displayed at (214) can be updated to reflect the most recent score indicative of mindfulness.

Figure 5:
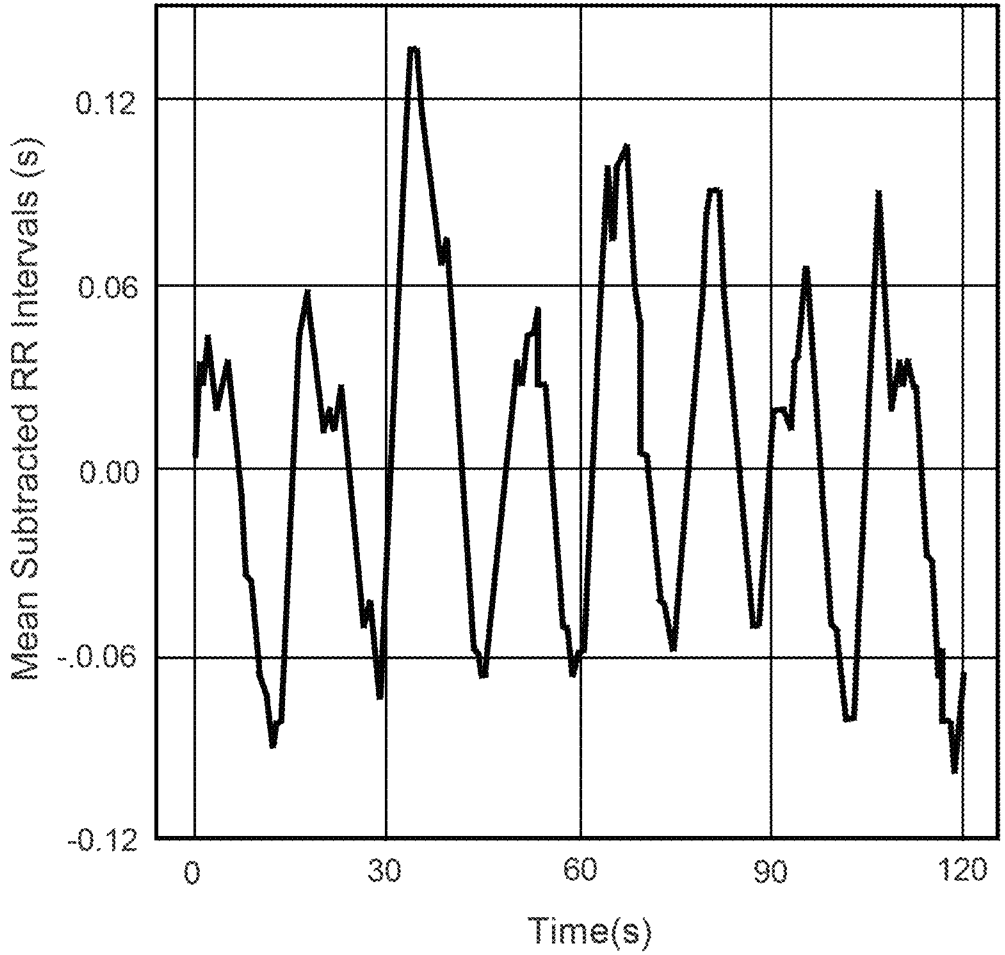
FIG. 5 depicts a graphical representation of heart rate variability data for a user over an interval of time according to an embodiment of the present disclosure.

Referring now to FIG. 5, a graphical representation of a segment of filtered HRV data for a user is provided according to embodiments of the present disclosure. As shown, the segment of filtered HRV data spans an interval of time (that is, 2-minutes) during which the respiration rate of the user is substantially constant. It should be understood that the segment of filtered HRV includes interbeat intervals detected over the interval of time.

Figure 6:
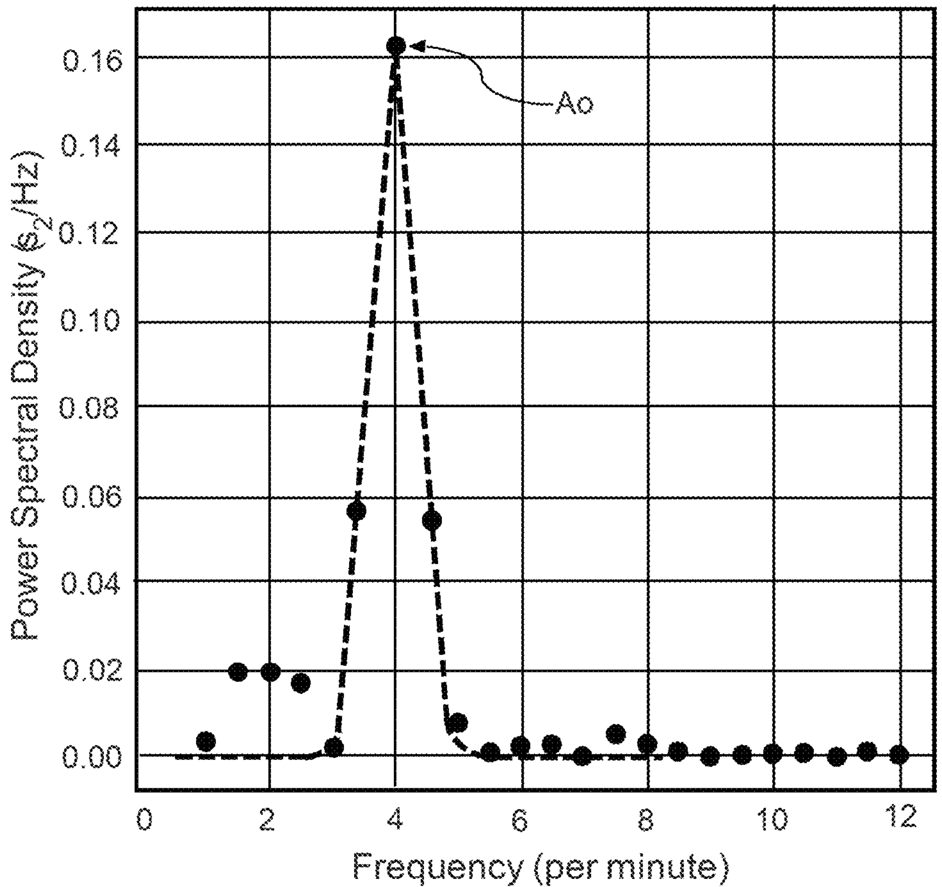
FIG. 6 depicts a graphical representation of a power spectral density of the heart rate variability data in FIG. 5 according to an embodiment of the present disclosure.

Referring now to FIG. 6, a graphical representation of a power spectral density of the filtered HRV of FIG. 5 is provided according to embodiments of the present disclosure. As shown, a peak amplitude Ao of the power spectral density is indicative of a respiration rate of the user. Furthermore, as discussed above with reference to FIG. 4, a Gaussian function (denoted by dashed line) can be fit to the peak amplitude Ao and the integral of the Gaussian function can be taken to determine the standard deviation of interbeat intervals in the segment of HRV data that are indicative of respiratory sinus arrhythmia. For instance, the area under the Gaussian function can be indicative of the standard deviation of interbeat intervals in the segment of HRV data that are indicative of respiratory sinus arrythmia. Accordingly, the integral of the Gaussian function can be taken to find the standard deviation of the interbeat intervals that are indicative of respiratory sinus arrythmia.

In some embodiments, the one or more processors performing the method discussed above with reference to FIG. 4 can be configured to determine whether the peak amplitude Ao of the power spectral density is in fact the peak. For instance, the one or more processors can be configured to subtract the fitted Gaussian function from the power spectral density function to obtain a residual function. The one or more processors can then determine a largest peak in the residual function with a range of frequencies that includes the frequency of the peak amplitude Ao of the power spectral density function. The one or more processors can be configured to determine a ratio of the peak amplitude Ao of the power spectral density function to the peak amplitude of the residual function. If the ratio exceeds a threshold value, the peak amplitude Ao of the power spectral density function is considered to be valid. Otherwise, the segment of the HRV data is discarded since the respiratory rate is not well defined.

Figure 7A:
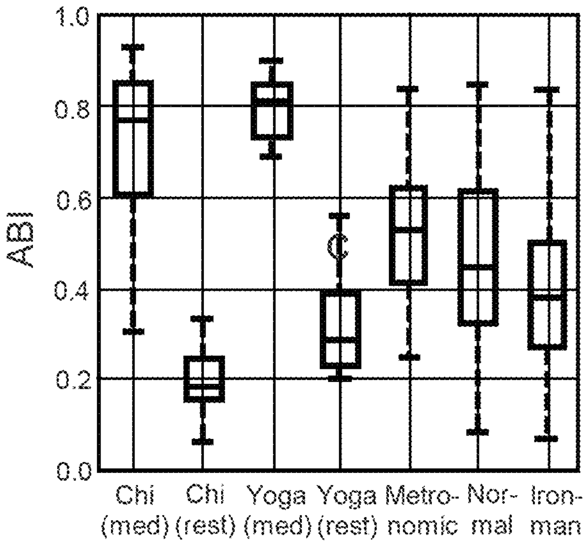
FIG. 7A depicts the ABI or score for each of the different groups during meditation and at rest.
Figure 7B:
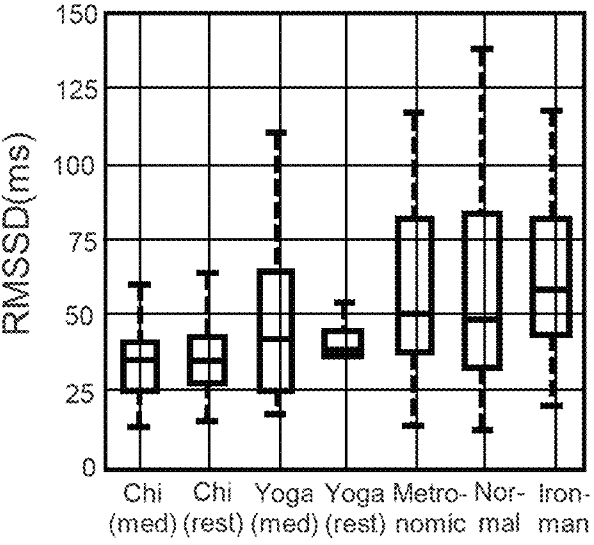
FIG. 7B depicts the root mean square of successive differences (RMSSD) for each of the different groups during meditation and at rest.
Figure 7C:
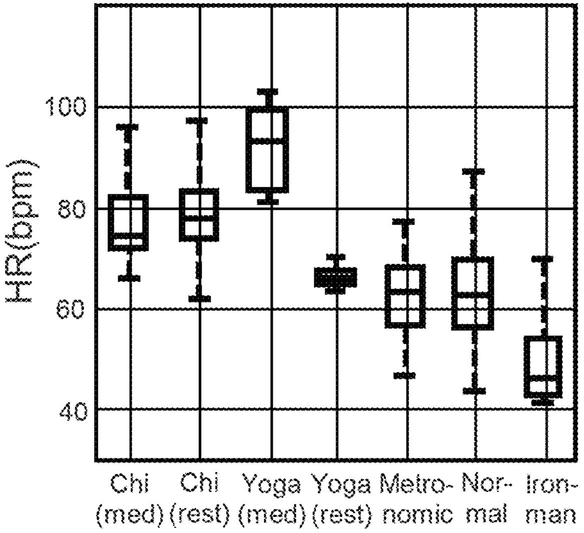
FIG. 7C depicts a heart rate for each of the different groups during meditation and at rest.
Figure 7D:
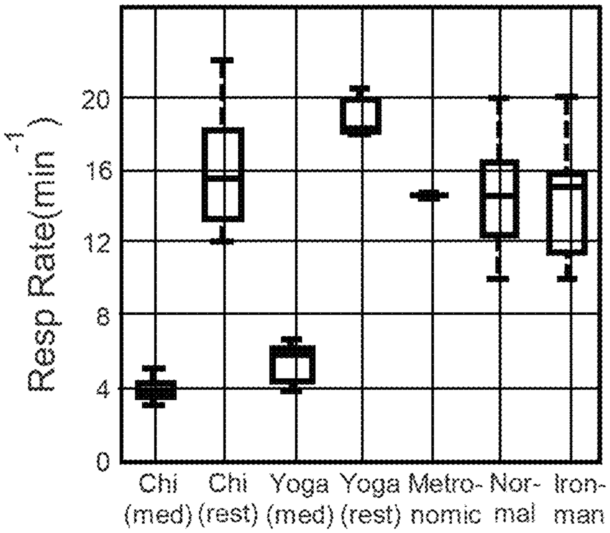
FIG. 7D depicts a respiration rate for each of the different groups during meditation and at rest.

Referring now to FIGS. 7A through 7D, graphical illustrations of the effectiveness of different metrics in determining mindfulness for a plurality of different groups or manners of breathing both during meditation and at rest is provided according to an embodiment of the present disclosure. FIG. 7A depicts the ABI or score for each of the different groups during meditation and at rest. FIG. 7B depicts the root mean square of successive differences (RMSSD) for each of the different groups during meditation and at rest. FIG. 7C depicts a heart rate for each of the different groups during meditation and at rest. FIG. 7D depicts a respiration rate for each of the different groups during meditation and at rest. As may be seen, the ABI (FIG. 7A) and respiration rate (FIG. 7D) are more sensitive than RMSSD (FIG. 7B) and heart rate (FIG. 7C).

Figure 8:
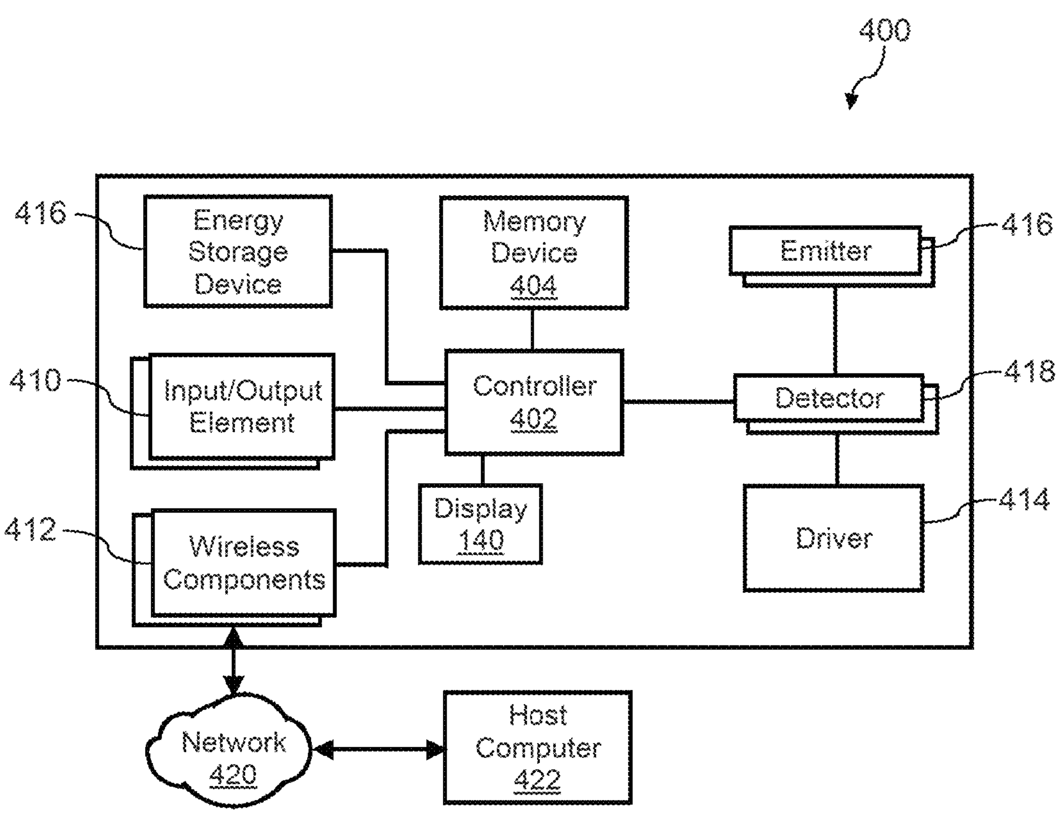
FIG. 8 depicts devices that are able to communicate with one another according to an embodiment of the present disclosure.

Referring now to FIG. 8, components of an example computing system 400 of the wearable computing device 100 that can be utilized in accordance with various embodiments are illustrated. In particular, as shown, the computing system 400 may also include at least one controller 402. Moreover, in an embodiment, the controller(s) 402 can be a central processing unit (CPU) or graphics processing unit (GPU) for executing instructions that can be stored in a memory device 404, such as flash memory or DRAM, among other such options. For example, in an embodiment, the memory device 404 may include RAM, ROM, FLASH memory, or other non-transitory digital data storage, and may include a control program comprising sequences of instructions which, when loaded from the memory device 404 and executed using the controller(s) 402, cause the controller(s) 402 to perform the functions that are described herein.

The computing system 400 can include many types of memory, data storage, or computer-readable media, such as data storage for program instructions for execution by the controller or any suitable processor. The same or separate storage can be used for images or data, a removable memory can be available for sharing information with other devices, and any number of communication approaches can be available for sharing with other devices. In addition, as shown, the computing system 400 includes the display 130, which may be a touch screen, organic light emitting diode (OLED), or liquid crystal display (LCD), although devices might convey information via other means, such as through audio speakers, projectors, or casting the display or streaming data to another device, such as a mobile phone, wherein an application on the mobile phone displays the data.

The computing system 400 can include one or more wireless networking components 412 operable to communicate with one or more electronic devices within a communication range of a particular wireless channel. The wireless channel can be any appropriate channel used to enable devices to communicate wirelessly, such as Bluetooth, cellular, NFC, Ultra-Wideband (UWB), or Wi-Fi channels. It should be understood that the computing system 400 can have one or more conventional wired communications connections as known in the art.

The computing system 400 also includes one or more energy storage devices 408, operable to be recharged through conventional plug-in approaches. In some embodiments, the computing system 400 can also include at least one additional I/O device 410 able to receive conventional input from a user. This conventional input can include, for example, a push button, touch pad, touch screen, wheel, joystick, keyboard, mouse, keypad, or any other such device or element whereby a user can input a command to the computing system 400. In some embodiments, the I/O device(s) 410 can be connected by a wireless infrared or Bluetooth or other link as well in some embodiments. In some embodiments, the computing system 400 can include a microphone or other audio capture element that accepts voice or other audio commands. In some embodiments, the I/O device(s) 410 can include one or more electrodes, optical sensors, barometric sensors (e.g., altimeter, etc.), and the like.

The computing system 400 can include a driver 414 and at least some combination of one or more emitters 416 and one or more detectors 418 for measuring data for one or more metrics of a human body, such as for a person wearing the wearable computing device 100. In some embodiments, for example, this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Further image capture elements may also include depth sensors. Methods for capturing images using a camera element with a computing device are well known in the art and will not be discussed herein in detail. It should be understood that image capture can be performed using a single image, multiple images, periodic imaging, continuous image capturing, image streaming, etc. Further, the computing system 400 can include the ability to start and/or stop image capture, such as when receiving a command from a user, application, or other device.

The emitters 416 and the detectors 418 may also be capable of being used, in one example, for obtaining optical photoplethysmogram (PPG) measurements. Some PPG technologies rely on detecting light at a single spatial location, or adding signals taken from two or more spatial locations. Both of these approaches result in a single spatial measurement from which the heart rate (HR) estimate (or other physiological metrics) can be determined. In some embodiments, a PPG device employs a single light source coupled to a single detector (i.e., a single light path). Alternatively, a PPG device may employ multiple light sources coupled to a single detector or multiple detectors (i.e., two or more light paths). In other embodiments, a PPG device employs multiple detectors coupled to a single light source or multiple light sources (i.e., two or more light paths). In some cases, the light source(s) may be configured to emit one or more of green, red, infrared (IR) light, as well as any other suitable wavelengths in the spectrum (such as long IR for metabolic monitoring). For example, a PPG device may employ a single light source and two or more light detectors each configured to detect a specific wavelength or wavelength range. In some cases, each detector is configured to detect a different wavelength or wavelength range from one another. In other cases, two or more detectors are configured to detect the same wavelength or wavelength range. In yet another case, one or more detectors configured to detect a specific wavelength or wavelength range different from one or more other detectors). In embodiments employing multiple light paths, the PPG device may determine an average of the signals resulting from the multiple light paths before determining an HR estimate or other physiological metrics.

Moreover, in an embodiment, the emitters 416 and detectors 418 may be coupled to the controller 402 directly or indirectly using driver circuitry by which the controller 402 may drive the emitters 416 and obtain signals from the detectors 418. The host computer 422 can communicate with the wireless networking components 412 via the one or more networks 420, which may include one or more local area networks, wide area networks. UWB, and/or internet works using any of terrestrial or satellite links. In some embodiments, the host computer 422 executes control programs and/or application.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method for determining mindfulness of a user performing a guided breathing exercise, the computer-implemented method comprising:

initiating the guided breathing exercise via a software application of a wearable computing device;

prompting the user to attain a desired respiration rate that results in respiratory sinus arrythmia for the user;

obtaining heart rate variability data of the user via one or more biometric sensors arranged on a bottom side of the wearable computing device and in contact with skin of the user performing the guided breathing exercise;

filtering the heart rate variability data to generate filtered heart rate variability data;

determining a first standard deviation of interbeat intervals included in a first segment of the filtered heart rate variability data and indicative of the respiratory sinus arrythmia for the user, the first segment spanning a discrete interval of time;

determining a second standard deviation of the interbeat intervals included in the first segment of the filtered heart rate variability data;

determining a score indicative of mindfulness of the user for the discrete interval of time based, at least in part, on the first standard deviation to the second standard deviation, wherein mindfulness is a state in which a parasympathetic branch of the user's autonomic nervous system (ANS) is more dominant than a sympathetic branch of the user's ANS;

determining an actual respiration rate of the user for the discrete interval of time based, at least in part, on the first segment of the filtered heart rate variability data; and causing a display screen of the wearable computing device worn by the user to display the score and the actual respiration rate while the user is performing the guided breathing exercise so as to notify the user whether the actual respiration rate is preventing the user from achieving mindfulness by deviating from the desired respiration rate.

2. The computer-implemented method of claim 1, wherein determining the score indicative of mindfulness of the user for the discrete interval of time includes determining the score based, at least in part, on a ratio of the first standard deviation to the second standard deviation.

3. The computer-implemented method of claim 1, wherein determining the first standard deviation includes:

applying a Fourier transform to the first segment of the filtered heart rate variability data to obtain a normalized power spectral density function;

determining a peak amplitude of the normalized power spectral density function, the peak amplitude being indicative of the respiration rate of the user, fitting a Gaussian function to the peak amplitude of the normalized power spectral density function; and determining the first standard deviation based, at least in part, on the Gaussian function.

4. The computer-implemented method of claim 3, wherein determining the first standard deviation based, at least in part, on the Gaussian function includes integrating the Gaussian function to determine an area under the Gaussian function.

5. The computer-implemented method of claim 1, wherein filtering the heart rate variability data includes applying a low-pass filter to the heart rate variability data.

6. The computer-implemented method of claim 1, wherein the discrete interval of time is about 2 minutes.

7. The computer-implemented method of claim 1, wherein:

the score indicates the user is being mindful when the score is greater than or equal to a first numerical value;

the score indicates the user is stressed when the score is less than a second numerical value that is smaller than the first numerical value.

8. A wearable computing device comprising:

a housing;

one or more biometric sensors arranged on a bottom side of the housing such that the one or more biometric sensors contact skin of a user when worn; and one or more processors configured to:

initiate the guided breathing exercise via a software application of the wearable computing device;

prompt the user to attain a desired respiration rate that results in respiratory sinus arrythmia for the user;

obtain, via the one or more biometric sensors, heart rate variability data of the user wearing the wearable computing device and performing a guided breathing exercise;

filter the heart rate variability data to generate filtered heart rate variability data;

determine a first standard deviation of interbeat intervals included in a first segment of the filtered heart rate variability data and indicative of the respiratory sinus arrythmia for the user, the first segment spanning a discrete interval of time;

determine a second standard deviation of all interbeat intervals included in the first segment of the filtered heart rate variability data;

determine a score indicative of mindfulness of the user for the discrete interval of time based, at least in part, on the first standard deviation to the second standard deviation, wherein mindfulness is a state in which a parasympathetic branch of the user's autonomic nervous system (ANS) is more dominant than a sympathetic branch of the user's ANS;

determine an actual respiration rate of the user for the discrete interval of time based, at least in part, on the first segment of the filtered heart rate variability data; and cause a display screen of the wearable computing device worn by the user to display the score and the actual respiration rate while the user is performing the guided breathing exercise so as to notify the user whether the actual respiration rate is preventing the user from achieving mindfulness by deviating from the desired respiration rate.

9. The wearable computing device of claim 8, wherein to determine the score indicative of mindfulness of the user, the one or more processors are configured to determine the score indicative of mindfulness of the user for the discrete interval of time based, at least in part, on a ratio of the first standard deviation to the second standard deviation.

10. The wearable computing device of claim 8, wherein to determine the first standard deviation, the one or more processors are configured to:

apply a Fourier transform to the first segment of the heart rate variability data to obtain a normalized power spectral density function;

determine a peak amplitude of the normalized power spectral density function, the peak amplitude being indicative of the respiration rate of the user, fit a Gaussian function to the peak amplitude of the normalized power spectral density function; and determine the first standard deviation based, at least in part, on the Gaussian function.

11. The wearable computing device of claim 10, wherein to determine the first standard deviation, the one or more processors are configured to integrate the Gaussian function over the discrete interval of time to determine an area under the Gaussian function.

12. The wearable computing device of claim 8, wherein to filter the heart rate variability data, the one or more processors are configured to apply a low-pass filter to the heart rate variability data.

13. The wearable computing device of claim 12, wherein the score indicates the user is being mindful when the score is greater than or equal to a first numerical value, and wherein the score indicates the user is stressed when the score is less than a second numerical value that is smaller than the first numerical value.

14. The wearable computing device of claim 8, wherein the score indicative of mindfulness of the user for the discrete interval of time ranges from 0 to 100.

15. A computer-implemented method for determining mindfulness of a user performing a guided breathing exercise, the method comprising:

initiating the guided breathing exercise via a software application of a wearable computing device;

prompting the user to attain a desired respiration rate that results in respiratory sinus arrythmia for the user;

obtaining heart rate variability data of the user via one or more biometric sensors arranged on a bottom side of the wearable computing device and in contact with skin of the user performing the guided breathing exercise;

determining a first standard deviation of interbeat intervals included in a first segment of the heart rate variability data and indicative of the respiratory sinus arrythmia for the user, the first segment spanning a discrete interval of time;

determining a second standard deviation of all interbeat intervals included in the first segment of the heart rate variability data;

determining a score indicative of mindfulness of the user for the discrete interval of time based, at least in part, on the first standard deviation to the second standard deviation, wherein mindfulness is a state in which a parasympathetic branch of the user's autonomic nervous system (ANS) is more dominant than a sympathetic branch of the user's ANS;

determining an actual respiration rate of the user for the discrete interval of time based, at least in part, on the first segment of the heart rate variability data; and causing a display screen of the wearable computing device worn by the user to display the score and the actual respiration rate while the user is performing the guided breathing exercise so as to notify the user whether the actual respiration rate is preventing the user from achieving mindfulness by deviating from the desired respiration rate.

16. The computer-implemented method of claim 15, wherein determining the score indicative of mindfulness of the user for the discrete interval of time includes determining a ratio of the first standard deviation to the second standard deviation.

* * * * *